(12) United States Patent
Gehner et al.

(10) Patent No.: US 6,684,719 B2
(45) Date of Patent: Feb. 3, 2004

(54) METHOD AND APPARATUS FOR MIXING GASES

(75) Inventors: Gerrick S. Gehner, Peoria, IL (US); Russel R. Graze, Jr., Dunlap, IL (US); Kartik G. Iyer, Dunlap, IL (US); Korby A. Koch, Rome, IL (US); Hemant P. Mallampalli, Normal, IL (US); John R. Wagner, Chillicothe, IL (US)

(73) Assignee: Caterpillar Inc, Peoria, IL (US)

( * ) Notice: Subject to any disclaimer, the term of this patent is extended or adjusted under 35 U.S.C. 154(b) by 0 days.

(21) Appl. No.: 10/137,370

(22) Filed: May 3, 2002

(65) Prior Publication Data

US 2003/0205096 A1 Nov. 6, 2003

(51) Int. Cl.[7] ................................................. G01N 1/00
(52) U.S. Cl. ........................................................ 73/863
(58) Field of Search ........................ 73/863.01–863.03, 73/863.11; 137/599.01, 599.03, 602, 896–898; 366/341, 107

(56) References Cited

U.S. PATENT DOCUMENTS

| | | | |
|---|---|---|---|
| 2,353,865 A | | 7/1944 | Armstrong |
| 3,699,814 A | | 10/1972 | Kaufman |
| 3,913,617 A | * | 10/1975 | van Laar et al. ......... 137/599.01 |
| 4,398,827 A | | 8/1983 | Dietrich |
| 4,647,212 A | * | 3/1987 | Hankison ................. 366/165.5 |
| 4,660,408 A | | 4/1987 | Lewis |
| 5,058,440 A | | 10/1991 | Graze, Jr. |
| 5,090,258 A | | 2/1992 | Yamasaki et al. |
| 5,129,412 A | | 7/1992 | Hendry |
| 5,184,501 A | | 2/1993 | Lewis et al. |
| 5,410,907 A | | 5/1995 | Ström et al. |
| 5,450,749 A | | 9/1995 | Ström et al. |
| 5,604,319 A | * | 2/1997 | Kohsaka et al. ......... 73/863.11 |
| 6,114,178 A | * | 9/2000 | Dezael et al. ................ 436/180 |
| 6,293,161 B1 | * | 9/2001 | Hanashiro et al. ....... 73/863.11 |
| 6,370,936 B1 | * | 4/2002 | Yamagishi et al. .......... 73/1.35 |

FOREIGN PATENT DOCUMENTS

| | | | |
|---|---|---|---|
| GB | 2 077 127 | | 12/1981 |
| IT | 531777 | * | 8/1955 ................. 137/897 |
| SU | 1408004 | | 7/1988 |

OTHER PUBLICATIONS

European Search Report dated Jul. 22, 2003.

* cited by examiner

*Primary Examiner*—Robert Raevis
(74) *Attorney, Agent, or Firm*—Finnegan, Henderson, Farabow, Garrett & Dunner

(57) ABSTRACT

A method and apparatus for mixing a first stream of gas with a second stream of gas is provided. The method includes introducing a first stream of gas into a first stream manifold and directing the first stream from the first stream manifold into a mixing chamber via a plurality of first stream passages flow coupled to the mixing chamber. A second stream of gas is directed into the mixing chamber via at least one second stream passage flow coupled to a first end of the mixing chamber. A combined stream is formed from the first and second streams, gradually converged, and discharged from the mixing chamber through a mixing chamber exit port.

12 Claims, 4 Drawing Sheets

METHOD AND APPARATUS FOR MIXING GASES

TECHNICAL FIELD

The present invention is directed to a method and an apparatus for mixing streams of gases to form a combined stream.

BACKGROUND

The federal government and other authorities regulate allowable exhaust emissions from gasoline and diesel engines for automobiles, trucks, and other vehicles, such as off-road construction or agricultural vehicles, in an effort to reduce pollution. In order to ensure compliance with these regulations, the exhaust gases of these engines must be tested or otherwise analyzed for undesirable combustion by-products, such as hydrocarbons, carbon monoxides, sulphates, and/or oxides of nitrogen. In general, testing is accomplished by introducing exhaust gases, diluting these exhaust gases with clean air, and obtaining samples after the exhaust gases and dilution air are properly mixed.

Dilution tunnels are one known type of device for collecting, diluting, cooling, and mixing exhaust gases with filtered, ambient, and conditioned air in a ratio of gas to air for sampling and analyzing. At one end, a typical dilution tunnel has one inlet for receiving exhaust gases and another inlet for receiving the filtered air. An orifice plate is typically placed downstream of the exhaust gas and air inlets in order to induce turbulent flow and facilitate mixing of the exhaust gas and diluting air. Downstream of the orifice plate a probe is located in the tunnel to collect a sample of the mixture for analysis. One problem with placing orifice plates, or other obstructions such as inlet pipes, in the stream is that they tend to collect and remove some of the particulate matter from the stream, which distorts the downstream samples. Moreover, abrupt changes in tunnel geometry may also cause particulate matter to collect on the tunnel walls. This particulate matter may build up on the plate or walls over time and then periodically flake off, further distorting the samples taken downstream.

Full dilution tunnels collect and dilute the entire exhaust gas flow from the engine being tested. Current EPA regulations recommend that the dilution tunnels be sized to permit development of turbulent flow (Reynold's number greater than 4000) and obtain a homogeneous mixture of the exhaust and dilution air at the sampling location. Depending upon the engine displacement, in order to meet this requirement, a typical full dilution tunnel diameter may be on the order of 203 to 610 mm (8 to 24 inches) and a typical tunnel length, which is usually ten times the diameter, may be on the order of 2032 to 6100 mm (80 to 240 inches). The tunnel diameter and length is sized to insure proper mixing of the exhaust gas with the diluting air prior to taking the sample. The larger the engine displacement, the larger the tunnel diameter and tunnel length must be to accommodate the greater flow of exhaust gas. Thus, dilution tunnels for large displacement engines may be very bulky, even taking up entire rooms.

U.S. Pat. No. 5,090,258 discloses a multiple flow-dividing dilution tunnel system. Dilution air is introduced at one end of the tunnel. Further downstream, a portion of an exhaust gas stream is introduced into the tunnel via an exhaust gas inlet pipe inserted into the stream of dilution air. Further downstream, but proximate the end of the exhaust gas inlet pipe, a plurality of nozzles are inserted into the stream of dilution air/exhaust gas for introducing more dilution air, in this instance, a controlled amount of pressurized dilution air. This introduction of pressurized dilution air is used to properly maintain the ratio of the rate of the divided exhaust gas introduced into the dilution tunnel via the exhaust gas inlet pipe to the rate of the total gas introduced into the system, even during pressure loss fluctuations. One drawback of this system is that it requires a complex control system for reacting to pressure fluctuations. Another drawback is that it also requires a complex system of piping, both for splitting the exhaust gas stream and for introducing the pressurized dilution air. A further drawback is that the exhaust inlet pipe is exposed to the dilution air stream prior to the exhaust gas exiting the inlet pipe, causing undesirable cooling of the exhaust gas prior to mixing.

The disclosed method and apparatus for mixing streams of gases solves one or more of the problems set forth above.

SUMMARY OF THE INVENTION

One aspect of the present invention is directed to a method of mixing a first stream of gas with a second stream of gas. The method includes introducing the first stream of gas into a first stream manifold and directing the first stream from the first stream manifold into a mixing chamber via a plurality of first stream passages flow coupled to the mixing chamber. The second stream of gas is directed into the mixing chamber via at least one second stream passage flow coupled to a first end of the mixing chamber. A combined stream is formed from the first and second streams, gradually converged, and discharged from the mixing chamber through a mixing chamber exit port.

In another aspect, the present invention is directed to an apparatus for mixing a first and second stream of gas. The apparatus includes a first stream manifold configured to receive the first stream of gas, and a first plurality of passages flow coupled to and extending from the first stream manifold. A mixing chamber having first and second ends is flow coupled to the first plurality of passages and configured to receive the second stream of gas at the first end. The mixing chamber has an exit port at the second end and a cross-section adjacent the second end which gradually converges as the distance to the exit port decreases.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the invention and together with the description, serve to explain the principles of the invention. In the drawings.

DETAILED DESCRIPTION

Figure 1:
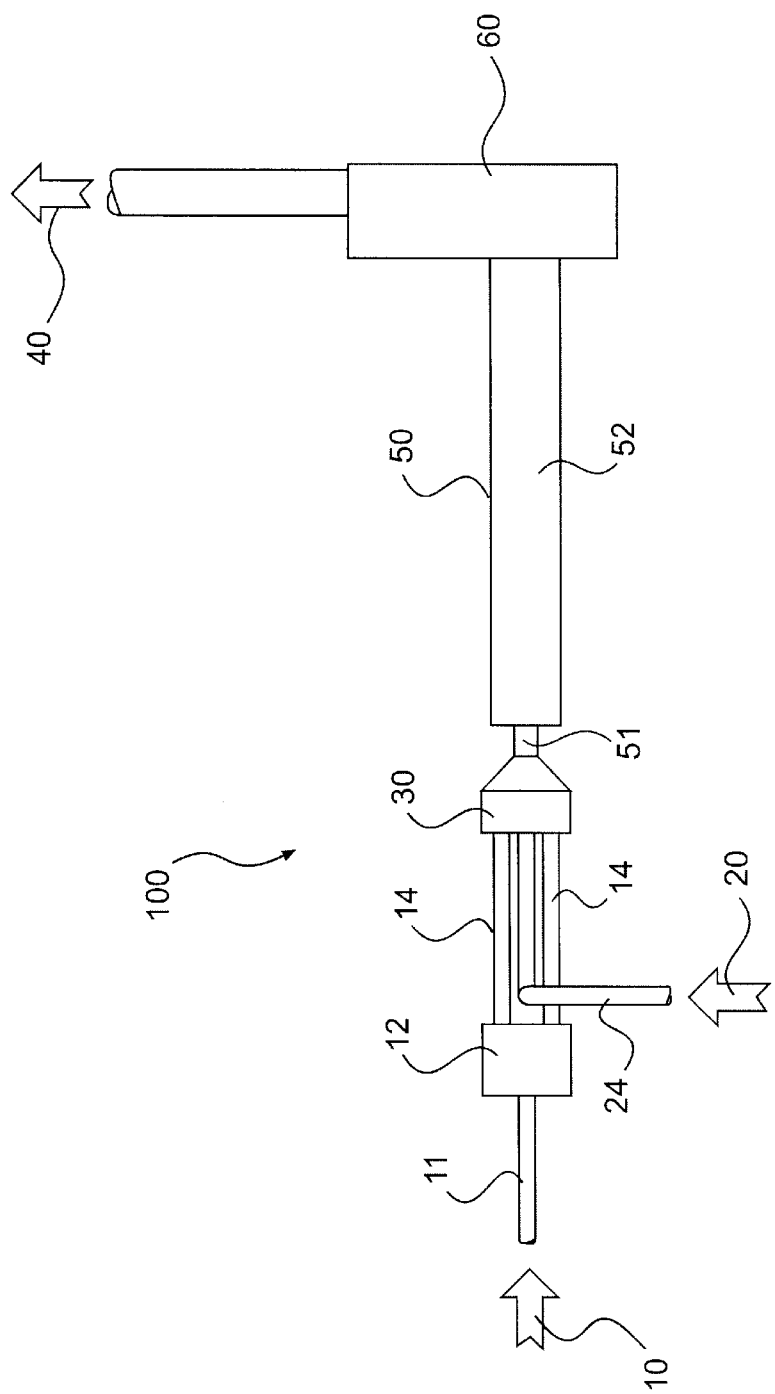
FIG. 1 is a schematic and diagrammatic illustration of an embodiment of an apparatus for mixing gases.

FIG. 1 shows an apparatus, designated generally by reference number 100, which includes a mixing chamber 30 receiving a first stream 10 and a second stream 20. In one embodiment, first stream 10 may be either a stream of exhaust gas or a stream of dilution gas, and second stream 20 may be the other of the stream of exhaust gas or dilution gas. For example, first stream 10 may be a stream of dilution gas and second stream 20 may be a stream of exhaust gas.

Thus, mixing chamber 30, which receives both first stream 10 and second stream 20, would receive, in this embodiment, both the stream of exhaust gas and the stream of dilution gas. The stream of exhaust gas, which may be generated by an engine, such as a diesel engine, contains particulate matter and/or other emissions that are to be measured. The stream of dilution gas may be conditioned air, i.e., air that is filtered, heated, cooled, humidified, de-humidified, etc.

In one embodiment, as shown in FIG. 1, apparatus 100 may include, among other components, first stream manifold 12, passages 14, 24, mixing chamber 30, and secondary mixing region 50. Each of these components may be designed and manufactured with no internal protuberances or projections that could collect particulate matter, if any, carried by the first and/or second streams 10, 20. Moreover, the internal wall surfaces of each of these components may be made of smooth materials, such as an electro-polished, passivated, stainless steel or other smooth, relatively non-stick materials, for minimizing the amount of particulate matter that could collect on the walls. In addition, these components may be assembled in a manner that minimizes the number of wall surfaces upon which the first and second streams 10, 20 impinge or that minimizes the angle of impingement.

Figure 2:
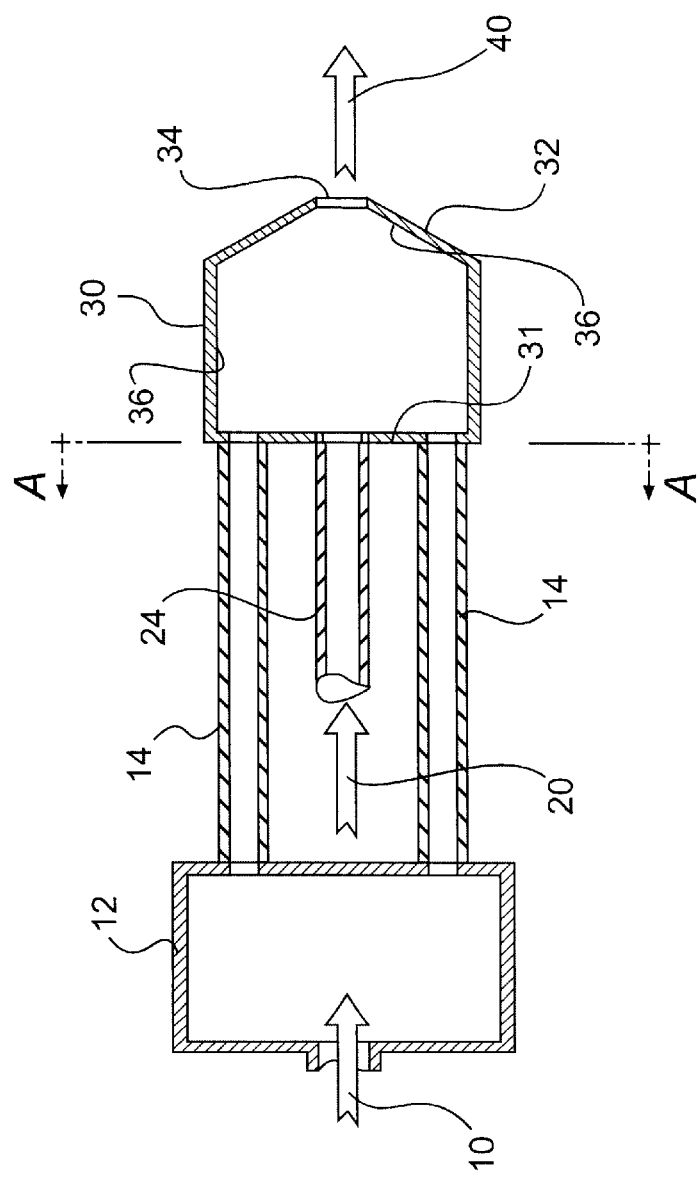
FIG. 2 is schematic cross-sectional illustration of a portion of the apparatus of FIG. 1 rotated 45 degrees so that at least two passages 14 and passage 24 lie in the viewing plane.

As shown in FIGS. 1 and 2, prior to entering mixing chamber 30, first stream 10 travels through an inlet pipe 11 and enters first stream manifold 12. First stream manifold 12 is used to evenly distribute first stream 10 into a plurality of passages 14. Passages 14 extend from first stream manifold 12 to mixing chamber 30 and are used to evenly introduce the flow of first stream 10 into mixing chamber 30. Additionally, passages 14 may be sized and configured to allow a well-developed flow to develop within first stream 10 as it flows through these passages. A well-developed flow has a steady state mean velocity profile, i.e., a mean velocity profile that does not change with distance in the flow direction. If a straight line passes through the diameter of a well-developed flow, the velocity at a each point of the line would be different. The velocity near the walls would be a minimum velocity, for instance, a zero velocity, while the velocity near the center of the passage would be a maximum. A well-developed flow generally arises in a long pipe if the flow is not subject to any protrusions, changes in cross-section, or other disturbances. For example, in FIG. 1, passages 14 are depicted as being smooth-walled, relatively thin, straight tubes sufficiently long to develop a well-developed turbulent flow prior to discharging first stream 10 into mixing chamber 30.

Second stream 20 is shown in FIGS. 1 and 2 entering mixing chamber 30 through second stream passage 24. Similar to passages 14, second stream passage 24 may be sized and configured to allow a turbulent flow to form within second stream 20 as it flows through passage 24. Passage 24 may be sized and configured such that, prior to entering mixing chamber 30, the flow of second stream 20 is a well-developed turbulent flow, with no separation at the passage walls. Passage 24 may be a smooth-walled, relatively long, narrow tube having, for example, two rounded ninety-degree bends.

Figure 3:
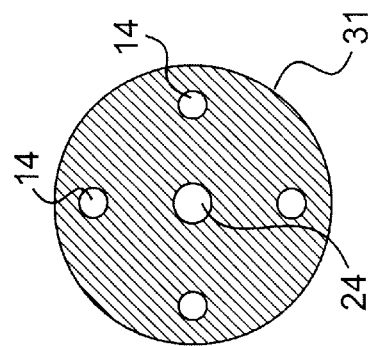
FIG. 3 is a cross-section of the apparatus of FIG. 2 taken at section A—A.

First stream 10 and second stream 20 are introduced into mixing chamber 30. Mixing chamber 30 has a first end 31 and a second end 32 opposite first end 31. As shown in FIGS. 2 and 3, first end 31 may be a flat wall. Both first and second streams 10, 20 are introduced into mixing chamber 30 at first end 31. As best shown in FIG. 2, passages 14 and passage 24 do not extend or protrude into mixing chamber, but end substantially flush with the wall of first end 31. This flush configuration allows for even mixing of first stream 10 with second stream 20, and ensures that neither the first stream nor the second stream is in contact with the passages of the other prior to discharging the streams into the mixing chamber. Isolating the first stream passage from the second stream prevents the second stream from prematurely and/or unevenly heating or cooling the first stream. Moreover, isolating the two streams from one another prior to their being discharged into mixing chamber 30 prevents the streams from becoming non-uniform or biased prior to discharge. For example, if the first stream was a hot exhaust gas stream and the second stream was a cool air stream, then contact between the passages of the hot exhaust gas stream and the cool air stream could cause the undesirable deposition of soot or other particulate matter on the walls of the exhaust gas stream passage due to thermophoretic effects. In addition, apparatus 100 or individual components of apparatus 100 may be insulated from the surrounding evironment and/or from one another to assist in minimizing thermophoretic effects.

As best shown in FIG. 3, the plurality of passages 14, which discharge first stream 10 into mixing chamber 30, are symmetrically positioned with respect to the cross-section of mixing chamber 30 and with respect to passage 24, which discharges second stream 20 into mixing chamber 30. Four passages 14 are shown, but any number of a plurality of passages may be utilized. A single passage 24 is shown, located in the center of first end 31, for discharging second stream 20 into mixing chamber 30. In alternative embodiments, more than one passage 24 may be provided. The symmetrical and distributed discharge of first stream 10 into mixing chamber 30 aids in the uniform and efficient mixing of first stream 10 with second stream 20.

Mixing chamber 30, as best shown in FIG. 2, is a smooth-walled chamber having no internal protuberances or projections, which could collect particulate matter, if any, carried by the first and/or second stream 10, 20.

Moreover, the internal wall surfaces 36 of mixing chamber 30 may be formed of a very smooth surface for minimizing the amount of particulate matter that collects on the walls. For instance, the internal wall surfaces 36 may be electro-polished, passivated, stainless steel or other smooth, relatively non-stick surfaces.

Within mixing chamber 30, first stream 10 and second stream 20 lose their separate identities and are combined into a combined stream 40. Combined stream 40 exits mixing chamber 30 through an exit port 34 located at second end 32. Combined stream 40 need not be a uniformly mixed stream by the time it exits mixing chamber 30 through exit port 34. Rather, combined stream 40 may include both first and second streams 10, 20 in a partially mixed state.

Second end 32 of mixing chamber 30 may include a portion wherein the cross-section gradually and symmetrically converges or necks down as the distance to exit port 34 decreases. A cross-section "gradually converges" when the cross-section becomes smaller and smaller in a series of steps or degrees, as opposed to an abrupt transition between two differently sized openings. As shown in FIGS. 1 and 2, the converging portion of second end 32 has the shape of a truncated cone. This converging portion may be part of a venturi-type nozzle. The gradual convergence of the walls of second end 32 provides a smooth, rather than an abrupt, transition to the reduced diameter of exit port 34. This smooth, gradual convergence is intended to prevent particles from collecting on the walls of end 32. Moreover, the symmetrical configuration of second end 32, as it converges, assists in the uniform mixing of combined stream 40.

As best shown in FIG. 1, downstream of mixing chamber 30, combined stream 40 may enter a secondary mixing region 50. Secondary mixing region 50 is depicted in FIG. 1 as having a short initial section 51 located immediately downstream of mixing chamber 30 and a longer cylindrical section 52 located downstream of section 51. The cross-sectional diameter of section 52 is greater than the cross-sectional diameter of section 51. An abrupt enlargement of the cross-sections, as shown in FIG. 1, may be advantageous because of manufacturing considerations. The abrupt enlargement may also enhance mixing.

Within secondary mixing region 50, uniform mixing, such as required for testing, of combined stream 40 may be achieved. A sampling device (not shown), such as any probe known to persons of ordinary skill in the art, may be located in secondary mixing region 50, such as, for example, adjacent to a downstream end thereof.

Downstream of secondary mixing region 50, combined stream 40 may be directed through a turn, for example, around a corner, to minimize the total length of the system. However, turning the stream may induce undesirable separation effects in combined stream 40 upstream of the turn, i.e., where the sampling probe may be located. A reservoir box 60, which may be a relatively large-volume chamber, may be flow coupled to secondary mixing region 50 at the downstream end of region 50. As shown in FIG. 1, combined stream 40 exits secondary mixing region 50 and is discharged into reservoir box 60. Reservoir box 60 provides a pressure drop in the downstream flow and serves to reduce any flow separation effects that might be induced in combined stream 40 adjacent the downstream end of secondary mixing region 50, while at the same time directing combined stream through a turn. Reservoir box 60 may be any chamber, including, for instance a porous baffle (not shown), that provides a pressure drop that reduces undesirable flow separation effects. Combined stream 40, as shown in FIG. 1, is then discharged from the system.

Figure 4:
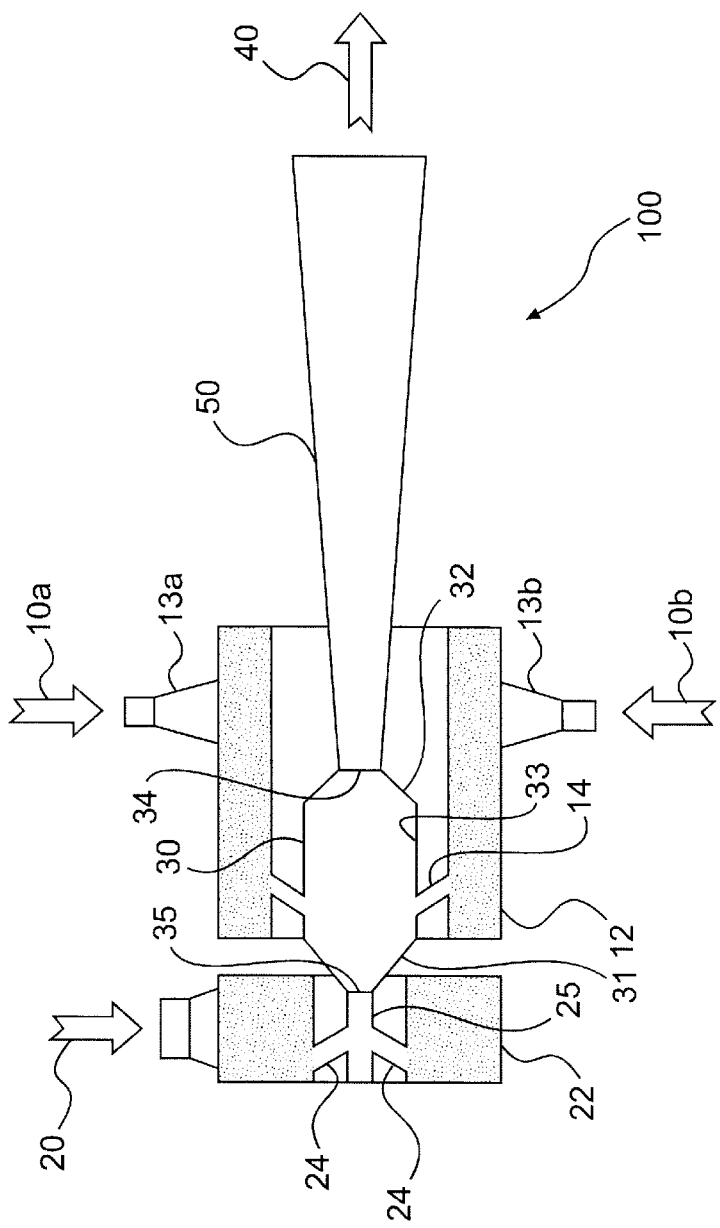
FIG. 4 is a schematic and diagrammatic illustration of another embodiment of an apparatus for mixing gases.

A second embodiment of an apparatus for mixing gases is illustrated in FIG. 4 and is also designated generally by reference number 100. As shown in FIG. 4, apparatus 100 includes a mixing chamber 30, a first stream manifold 12, a second stream manifold 22, and a secondary mixing region 50.

Figure 5:
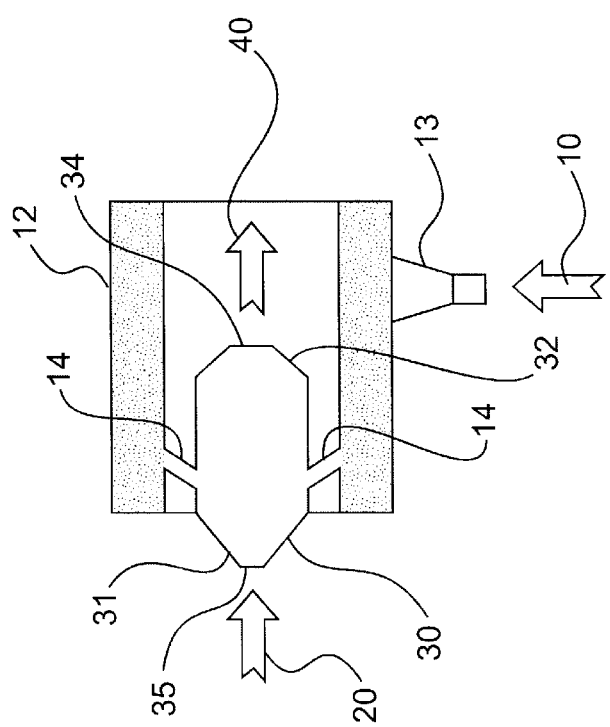
FIG. 5 is schematic and diagrammatic illustration of a further embodiment of an apparatus for mixing gases.

First stream manifold 12 may be configured as an annular chamber encircling mixing chamber 30, as shown in FIGS. 4 and 5. FIG. 4 illustrates an embodiment which is configured to receive two alternative first streams 10a, 10b. In this embodiment, first stream manifold 12 may receive either first stream 10a or first stream 10b through entrance ports 13a, 13b, respectively, located on opposite sides of annular manifold 12. Alternatively, the embodiment illustrated in FIG. 5 is configured to receive only one first stream, first stream 10. As shown in FIG. 5, first stream manifold 12 has only a single entrance port 13 for receiving first stream 10.

Entrance ports 13, 13a, 13b may include diffuser sections for slowing the flow of first streams 10, 10a, 10b, respectively. Diffuser sections may inhibit the impingement of first streams 10, 10a, 10b on the wall of first stream manifold 12 opposite the entrance ports 13, 13a, 13b, thereby, for instance, inhibiting any particulate matter that may be carried by streams 10, 10a, 10b from collecting or being deposited on the wall of first stream manifold 12. First stream manifold 12 may be formed with smooth internal wall surfaces to assist in minimizing the deposition of particulate matter on the walls.

A plurality of first stream passages 14 are flow coupled to and extend between first stream manifold 12 and mixing chamber 30. As shown in FIGS. 4 and 5, passages 14 extend radially between annular manifold 12 and centrally located mixing chamber 30. In this configuration, passages 14 allow first stream 10 to enter mixing chamber 30 adjacent first end 31. Passages 14 need not lie in a plane perpendicular to a central, longitudinal axis of the annular manifold and the mixing chamber. Rather, as shown, passages 14 may be angled out of this perpendicular plane.

Mixing chamber 30, as best shown in FIG. 5, may have a first end 31, having an entrance port 35 and walls which gradually diverge as the distance from entrance port 35 increases. Mixing chamber 30 may also have a second end 32, having an exit port 34 and walls which gradually converge as the distance from exit port 34 decreases.

Second stream 20 enters second stream manifold 22 prior to entering mixing chamber 30 via entrance port 35. Second stream manifold 22 may be an annular manifold similar to annular manifold 12 as shown in FIGS. 4 and 5, or second stream manifold 22 may be similar to first manifold 12 as shown in FIGS. 1 and 2. As shown in FIGS. 4 and 5, second stream 20 is discharged from annular manifold 22, via passages 24 into a central tubular region 25, which is flow coupled to entrance port 35 of mixing chamber 30.

Within mixing chamber 30 of FIGS. 4 and 5, as with mixing chamber 30 of FIGS. 1 and 2, first stream 10 and second stream 20 lose their separate identities and are combined into a combined stream 40, which exits mixing chamber 30 through exit port 34. Secondary mixing region 50 is flow coupled to mixing chamber 30 and receives combined stream 40. As shown in FIG. 4, secondary mixing region 50 gradually diverges as the distance from exit port 34 increases. This gradual divergence causes a gradual pressure drop in combined stream 40. Adjacent the downstream end of secondary mixing region 50, a sampling device (not shown) may be located in order to collect samples of a fully mixed combined stream 40.

INDUSTRIAL APPLICABILITY

The Environmental Protection Agency (EPA) requires transient emissions tests to be conducted for on-highway diesel engines. When utilizing a full dilution tunnel system, the EPA regulations (for instance, 40 CFR, Chapter 1, § 83.1310) require that the raw diesel engine exhaust be mixed or diluted with clean air in order to reduce the overall temperature of the exhaust levels. These EPA regulations require good mixing over the entire cross-section of the diluted flow of exhaust at the point where the emission samples are collected.

The apparatus and method provided may be used for mixing a first gas with a second gas prior to sampling a combined stream of the gases, in order to, for example, efficiently test exhaust gas samples for compliance with the EPA pollution regulations. In one exemplary use, the exhaust pipe of a diesel engine could be flow coupled to passage 24 as shown in FIG. 1. Exhaust gases from the diesel engine flow through passage 24, becoming a well-developed flow, which is introduced into mixing chamber 30. Minimal wall-separation of the exhaust flow is achieved, for instance, by providing two ninety-degree bends in passage 24 in three-dimensions. These bends allow the exhaust stream to be introduced into mixing chamber 30 in a minimal space, while at the same time allowing the exhaust stream flow to straighten and become a well-developed flow very quickly.

A source of conditioned dilution air could be flow coupled to inlet pipe 11, also as shown in FIG. 1. The dilution air flows into manifold 12 and then is distributed through the four passages 14 into mixing chamber 30. As the dilution air travels through passages 14, a well-developed flow is created in each passage, prior to being introduced into mixing chamber 30.

Passage 24, which carries the exhaust gas, is never in contact with the dilution air stream. Similarly, the exhaust gas stream never contacts passages 14, which carry the dilution air. Isolating these passages from the opposing streams prevents the possibility of pre-cooling the exhaust stream prior to its discharge into mixing chamber 30, which could lead to soot deposition on the walls of passage 24, and also prevents the possibility of the streams losing their well-developed flow profiles. Moreover, isolating these passages from the opposing streams greatly simplifies insulation concerns.

Apparatus 100 includes components, for instance, passages 14, manifold 12, passage 24, mixing chamber 30, secondary mixing region 50, etc., that have smooth internal walls, i.e., walls having surfaces that are not rough, to minimize the deposition of particulate matter on the internal wall surfaces. In addition, these components are free of any internal projections, such a inlet pipes, or other structures, such as baffles or orifice plates, extending from the internal walls into the flows. So, for instance, minimal particulate matter from the exhaust gas is deposited on surfaces within mixing chamber 30, because mixing chamber 30 has no projections, edges, or other structure extending into the flow stream. Moreover, if smooth, electro-polished, passivated, stainless steel is used to form the internal surfaces of mixing chamber 30 or other components of apparatus 100, the deposition of particulate matter on the internal surfaces of apparatus 100 may be minimized.

Within mixing chamber 30, the exhaust gas and the dilution air begin to mix in a uniform manner into a combined stream 40. Prior to exiting mixing chamber 30 through exit port 34, combined stream 40 travels through a converged portion of mixing chamber 30. This converged or necked down portion of mixing chamber 30 causes the velocity and the pressure of combined stream 40 to increase, and facilitates quick and uniform mixing of the combined stream. Downstream of mixing chamber 30, combined stream 40 travels through a cylindrical, venturi type, or similar type of secondary mixing region 50 to finalize the uniform mixing of the exhaust gas with the dilution air prior to a portion of the combined stream being collected for sampling purposes.

Even for large output engines, such as engines rated between 150 and 750 horsepower, apparatus 100, because of its compact size relative to existing full dilution tunnels, may be designed to fit into the same room that also houses the engine. For instance, apparatus 100 may be designed with pipes being no more than 0.64 meters (24 inches) in diameter. Finally, apparatus 100 may be designed to allow the use of standard pipes and standard-pipe fittings, thus, minimizing the use of specially built parts and substantially decreasing the cost of manufacture.

The disclosed system may also be utilized with dual test cells, thereby providing an even more compact and efficient system. As an example of the use of the embodiment shown in FIG. 4, a first test chamber (not shown) may be located adjacent apparatus 100 and may contain a first stream source (not shown). For instance, a diesel engine emitting a first stream 10a of an exhaust gas may be the first stream source. This first stream source may be flow coupled to entrance port 13a. A second test chamber (not shown) with a second stream source (not shown) may be located on the other side of apparatus 100. Second stream source may be a second diesel engine emitting a stream of exhaust gas as alternative first stream 10b. This second exhaust gas source producing alternative first stream 10b may be flow coupled to entrance port 13b. Thus, the embodiment with two entrance ports, shown in FIG. 4, may service two separate test chambers. In a first test, entrance port 13a may be opened, allowing first stream 10a to flow into manifold 12, while entrance port 13b may be closed, blocking the flow of alternative first stream 10b into manifold 12. In a subsequent test, entrance port 13b may be opened and entrance port 13a may be closed.

It will be apparent to persons of ordinary skill in the art that various modifications and variations can be made in the method and apparatus for mixing gases of the present invention without departing from the scope or spirit of the invention. Additionally, other embodiments of the invention may be apparent to persons of ordinary skill in the art from consideration of the specification and practice of the invention disclosed herein. It is intended that the specification and examples be considered as exemplary only, with a true scope and spirit of the invention being indicated by the following claims and their equivalents.

What is claimed is:

1. A method of mixing a first stream of gas with a second stream of gas, comprising:

introducing a first stream of gas into a first stream manifold;

directing the first stream from the first stream manifold into a mixing chamber via a plurality of first stream passages flow coupled to the mixing chamber;

directing a second stream of gas into the mixing chamber via at least one second stream passage flow coupled to a first end of the mixing chamber;

introducing the second stream into a second stream manifold, and wherein directing the second stream includes directing the second stream from the second stream manifold via a plurality of second stream passages flow coupled to the mixing chamber;

forming a combined stream from the first and second streams;

gradually converging the combined stream; and discharging the converged combined stream from the mixing chamber through a mixing chamber exit port.

2. The method of claim 1, further including:

expanding the converged combined stream downstream from the exit port.

3. The method of claim 1, further including:

developing a substantially well-developed flow of the first stream within the plurality of first stream passages.

4. The method of claim 3, further including:

developing a substantially well-developed flow of the second stream within the at least one second stream passage.

5. The method of claim 1, wherein the first stream is one of a stream of dilution air and a stream of exhaust gas from an engine, and the second stream is the other of the stream of dilution air and the stream of exhaust gas from an engine.

6. The method of claim 5, further including:
sampling the combined stream for compliance with emission standards.

7. An apparatus for mixing a first and a second stream of gas, comprising:
a first stream manifold configured to receive the first stream of gas;
a first plurality of passages flow coupled to and extending from the first stream manifold;
a mixing chamber having first and second ends, the mixing chamber flow coupled to the first plurality of passages and configured to receive the second stream of gas at the first end, the mixing chamber having an exit port at the second end and a cross-section adjacent the second end which gradually converges as the distance to the exit port decreases;
a second stream manifold flow coupled to the second stream of gas; and
a second plurality of passages flow coupled to and extending between the second stream manifold and the mixing chamber,
wherein the first and second plurality of passages do not substantially extend into the mixing chamber.

8. The apparatus of claim 7, further including:
a secondary mixing region flow coupled to the mixing chamber downstream of the exit port, wherein the secondary mixing region has a cross-section that gradually increases as the distance from the exit port increases.

9. The apparatus of claim 8, further including:
a second stream passage flow coupled to the mixing chamber at the first end and adapted to discharge the second stream of gas into the mixing chamber,
wherein the first stream manifold, the plurality of passages, the second stream passage, the mixing chamber, and the secondary mixing region have smooth walls, and
wherein at least the second stream passage, the mixing chamber, and the secondary mixing region are insulated.

10. The apparatus of claim 7, wherein the mixing chamber has internal wall surfaces formed of electro-polished, passivated, stainless steel.

11. The apparatus of claim 7, wherein the mixing chamber has smooth internal walls and no projections extending inwardly from the internal walls.

12. The apparatus of claim 7, wherein the first and second stream manifolds are annular chambers.

* * * * *

UNITED STATES PATENT AND TRADEMARK OFFICE
CERTIFICATE OF CORRECTION

PATENT NO. : 6,684,719 B2
DATED : February 3, 2004
INVENTOR(S) : Gerrick S. Gehner et al.

It is certified that error appears in the above-identified patent and that said Letters Patent is hereby corrected as shown below:

<u>Title page,</u>
Item [75], Inventors, "John R. Wagner" should be -- John E. Wagner --

Signed and Sealed this

Eighth Day of June, 2004

JON W. DUDAS
*Acting Director of the United States Patent and Trademark Office*